United States Patent [19]

Shibata et al.

[11] Patent Number: 4,581,377
[45] Date of Patent: Apr. 8, 1986

[54] FLUORENE DERIVATIVES

[75] Inventors: Yoshihisa Shibata, Kameoka; Yoshihiko Yoshimoto, Kusatsu, both of Japan

[73] Assignee: Nippon Shinyaku Co., Ltd., Japan

[21] Appl. No.: 669,455

[22] Filed: Nov. 7, 1984

[30] Foreign Application Priority Data

Nov. 9, 1983 [JP] Japan ................................ 58-211373

[51] Int. Cl.[4] ..................... A61K 31/12; C07C 49/792
[52] U.S. Cl. ..................................... 514/680; 568/633; 568/808; 568/705; 568/326; 568/306; 560/255; 564/322; 514/546; 514/656; 514/676; 514/719; 514/729; 514/727
[58] Field of Search ............... 424/331, 330, 311, 343; 568/326, 308, 705, 808, 633, 306; 560/255; 564/427, 322; 514/680, 546, 656, 676, 719, 729, 727; 562/255

[56] References Cited

U.S. PATENT DOCUMENTS 3,903,145  9/1975  Levine et al. ........................ 568/808
3,975,540  8/1976  Nelson et al. ....................... 568/326
4,011,266  3/1977  Pearson et al. ..................... 568/326
4,216,232  8/1980  Cole et al. .......................... 424/331
4,393,079  7/1983  Cole et al. .......................... 568/808

FOREIGN PATENT DOCUMENTS 760986  11/1956  United Kingdom ................ 568/326

Primary Examiner—James H. Reamer
Attorney, Agent, or Firm—Jacobs & Jacobs

[57] ABSTRACT

Compounds of formula I below are useful as anti-inflammatory, analgesic and/or anti-pyretic agents:

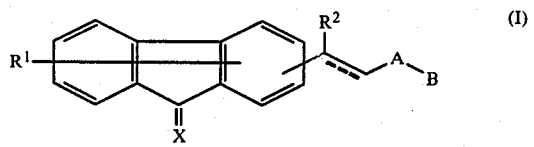

in which $R^1$ is hydrogen, nitro, amino, hydroxyl, alkoxy of one to four carbon atoms, alkyl of one to four carbon atoms or halogen; $R^2$ is hydrogen or alkyl of one to four carbon atoms;        is a saturated or unsaturated bond; A is CO, CHOH, $C(R^5)OH$ or $CHOCOR^6$, where $R^5$ and $R^6$ are alkyl of one to four carbon atoms; B is alkyl of one to twelve carbon atoms; and X is $H_2$ or O.

20 Claims, No Drawings

FLUORENE DERIVATIVES

The present invention relates to compounds, useful in anti-inflammatory, analgesic and/or anti-pyretic agents, having the general formula:

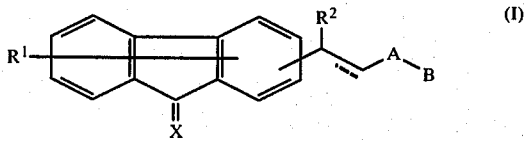

in which $R^1$ is hydrogen, nitro, amino, hydroxyl, alkoxy of one to four carbon atoms, alkyl of one to four carbon atoms or halogen; $R^2$ is hydrogen or alkyl of one to four carbon atoms; ═══ is a saturated or unsaturated bond; A is CO, CHOH, $C(R^5)OH$ or $CHOCOR^6$, where $R^5$ and $R^6$ are alkyl of one to four carbon atoms; B is alkyl of one to twelve carbon atoms; an X is $H_2$ or O. As used herein, alkyl and alkoxy include branched and straight chain alkyl and alkoxy of the defined carbon atom content. Preferably, halogen is fluorine and chlorine, but other halogen, e.g. bromine and iodine, may be used.

Compounds (I) are useful in the treatment of inflammation, such as rheumatic arthritis and bone arthritis, for relieving pain, such as caused by rheumatism and other inflammations, and for reducing fever, in animals, including humans. The compounds of the present invention cause little if any disorders of the digestive organs and have long lasting therapeutic activity.

The present invention also relates to a method of obtaining an anti-inflammatory, analgesic and/or anti-pyretic effect in an animal, including humans, in need thereof, which comprises administering to such animal an anti-inflammatory, analgesic and/or anti-pyretic effective amount of compound (I) of the present invention.

The present invention also includes a pharmaceutical composition, which comprises an anti-inflammatory, analgesic and/or anti-pyretic effective amount of compound (I) of the present invention in combination with a pharmaceutically acceptable carrier.

Compounds (I) of the present invention can be manufactured using substituted fluorene derivatives as intermediates. These substituted derivatives can be easily manufactured using commericially available fluorene and fluorenecarboxaldehyde as starting materials by known methods such as that given in Organic Synthesis Collective II, page 447; ibid. Collective V, page 30; Preparative Organic Chemistry, page 258 and page 343; and Helvetica Chimica Acta, 56(1), 280(1973).

In more detail, compounds (I) of the present invention may be manufactured by two routes. Thus, route A is a method in which desired substituents are introduced into the fluorene ring followed by successive introduction of side chains given in the general formula (I) and route B is a method in which side chains given in the general formula (I) are first introduced in fluorene followed by introduction of desired substituent.

Route A will be further illustrated as follows. Thus, introduction of alkyl, amino, alkoxy, halogen and other substituents into the fluorene ring can be easily achieved by known methods such as that disclosed in Organic Synthesis Collective II, page 447; Organic Synthesis Collective V, page 30; and Preparative Organic Chemistry, page 258 and page 343. Then the fluorene compounds with such a substituent is transformed to various substituted fluorene-2-carboxaldehydes by known formylation methods such as that given in Chemische Berichte, 93, page 83 (1960).

Such aldehydes are then made to react with methyl ketones such as, for example, acetone and equivalents thereof to manufacture compounds (I) in which the side chain is —CH═CHCOB (enone group). As equivalents of methyl ketone, acylmethylidene triphenylphosphoran may, for instance, be suitably applied. The reaction may preferably be carried out in inert aromatic hydrocarbons such as benzene or in ether type solvents such as, for example, tetrahydrofuran, ethyleneglycol or dimethyl ether by heating usually at 50° to 150° C., preferably at 80° to 120° C., an equimolar mixture of starting aldehyde and acetyl methylidene triphenylphosphoran.

After the reaction, the desired compounds can be isolated from a reaction mixture and purified by known techniques such as, for example, concentration, extraction with a solvent, transferring to other solvents, crystallization, ion exchange operation, adsorption, partition chromatography and the like.

Incidentally, the condensation of various aldehydes with methyl ketones such as acetone can be done in the presence of alcoholic or aqueous solution of alkali or alkali earth metal hydroxide (such as, for example, aqueous solution of sodium hydroixde or potassium hydroxide), aluminum alcoholate, piperidine acetate or basic ion exchanger. In order to prevent the reaction of two moles of aldehyde with one more of methyl ketone such as acetone in the above reaction, it is recommended to use 5 to 100 times as more as moles of methyl ketone to the starting aldehyde and to conduct the reaction at −10° to 60° C. in general.

Examples of catalysts applicable in the condensation reaction are acids, particularly mineral acids, and the use of hydrochloric acid or hydrobromic acid and an aqueous or alcoholic solutions thereof is preferred.

The resulting compounds having enone such as, for example, butenone group are then treated under various reductive conditions to afford compounds represented by the general formula (I) in which enol group such as butenol group (—CH:CHCH(OH)CH₃), ketone such as butanone group (—CH₂CH₂COCH₃) or alcohol such as butanol group (—CH₂CH₂CH(OH)CH₃) is present.

For instance, compounds having a butenol group are manufactured by treating the corresponding compounds having a butenone group with sodium borohydride ($NaBH_4$) at not higher than 10° C. using alcohols as solvents in the presence of cerium compounds, preferably, in the presence of equimolar $CeCl_3.7H_2O$.

Compounds having butanone group are manufactured by subjecting a double bond of the corresponding compound having a butenone group to hydrogenation.

Hydrogenation can be conducted by a catalytic reduction in the presence of metal catalysts such as, for example, Raney nickel, Raney cobalt, palladium carbon, platinum oxide or the like and it is recommended to cease the reaction when one to 1.2 equivalents of hydrogen is absorbed thereto. As to solvents, methanol, ethanol, isopropanol, aromatic hydrocarbons (such as benzene and the like), dioxane, lower aliphatic carboxylic acid esters (such as ethyl acetate, methyl acetate and the like), or a mixture thereof are applicable. The reaction is preferably conducted at 0° to 70° C. and 1 to 5 atmospheric pressure.

Compounds having butanol group are manufactured by, for example, treating the corresponding compounds having butanone group with metal hydrides such as, for example, sodium borohydride, lithium aluminum hydride and derivatives thereof (sodium borohydride being preferred) using alcohols as solvents. Reaction under the reductive condition according to Bouveault-Blanc reaction is also possible to achieve the purpose.

Route B will now be illustrated as hereunder.

Thus, Route B is another method in which a side chain is first introduced into fluorene and then substituents are introduced into the fluorene ring for the manufacture of the compounds represented by the general formula (I).

For example, fluoreneketones manufactured by the route A such as, for example, 4-(2-fluorenyl)-butan-2-one (compound of Example 3) is, for instance, subjected to nitration under conventional reaction condition such as that given in the example to give nitro-fluoreneketones such as, for example, 4-(7-nitro-2-fluorenyl)-butan-2-one (compound of Example 4).

Nitro groups in said compounds can be converted to amino groups such as that, for example, the compound of Example 4 is made to react with hydrogen using platinum oxide as a catalyst. The resulting aminated fluorene ketones such as, for example, 4-(7-amino-2-fluorenyl)-butan-2-one are made to react with sodium nitrite usually at 0° to 10° C. followed by treating with sulphuric acid to give nuclear hydroxylated fluorenyl ketones such as, for example, 4-(7-hydroxy-2-fluorenyl)-butan-2-one. Alternatively, amino compounds are made to react with sodium nitrite and then treated with, for example, cuprous halide (such as cuprous chloride) at 0° to 20° C. or with an aqueous solution of cuprous halide under reflux to afford halogenated fluorene ketones such as, for example, 4-(7-halo-2-fluorenyl)-butan-2-ones.

Hydroxylated fluorene ketones such as, for example, 4-(7-hydroxy-2-fluorenyl)-butan-2-one are made to react with alkyl halides such as methyl iodide in the presence of bases such as potassium carbonate in a solvent such as acetone to give alkoxylated fluorene ketones such as, for example, 4-(7-methoxy-2-fluorenyl)-butan-2-one.

Various ketone type compounds as manufactured by and in the above-given methods can be converted to the corresponding alcohol type ones by the already given reaction operations. Then, the ketone type compounds are made to react with oxidizing agents such as potassium permanganate in a solvent such as pyridine at 10° to 60° C. to give the corresponding 9-oxo derivatives.

Hydroxyl group in the alcohol type compound is first protected by suitable group such as acetyl group, then its 9-position is oxidized, and the protective group is detached to give the corresponding 9-oxo derivatives.

The enone type compounds are made to react with a Grignard reagent (R″Mg-halogen) in an ether type solvent such as ether or tetrahydrofuran preferably in the presence of cuprous salt such as cuprous iodide or they are made to react with dialkyl copper lithium in place of cuprous salt and Grignard reagent to give compounds in which an alkyl group is substituted at the carbon atom which is a member of the side chain and is directly bonded with the fluorene. (R″ is alkyl of 1 to 4 carbon atoms).

When the ketone type compounds are made to react with Grignard reagent (R″Mg-halogen), the alcohol type compounds in which an alkyl group is substituted at the carbon to which hydroxyl group is bonded are manufactured.

Of course, the alcohol type compounds can be converted to the corresponding alkoxy compounds having the group —OR⁶, by known means.

Routes A and B may be schematically shown as follows:

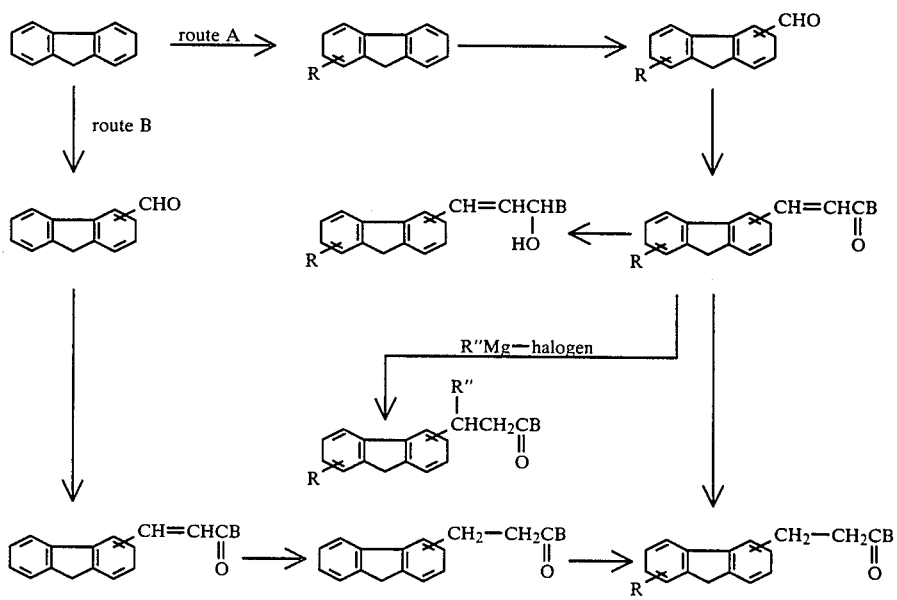

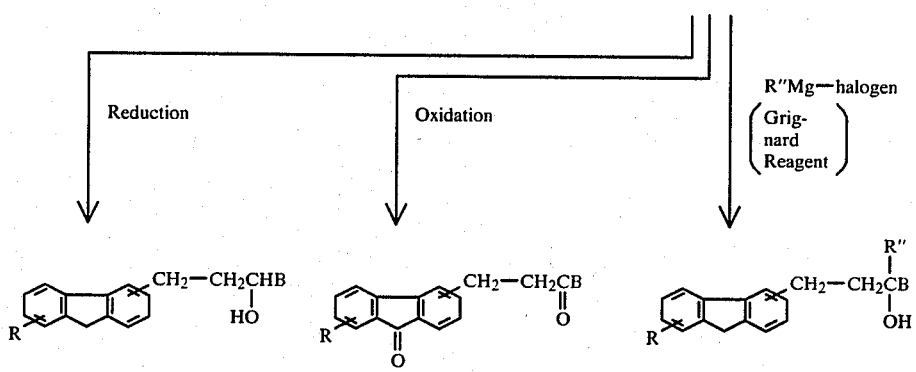

In its broadest terms, the present invention provides a method of manufacturing compounds (I) of the invention:

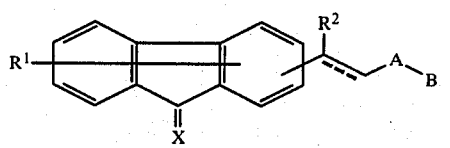

wherein $R^1$, $R^2$, X, A and B are as defined above, wherein a compound of formula (II)

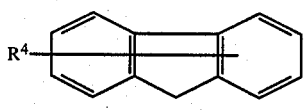

wherein $R^4$ is hydrogen, amino, hydroxy, alkoxy of 1 to 4 carbon atoms, alkyl of 1 to 4 carbon atoms or halogen, is formylated to give substituted or unsubstituted fluorene-2-carboxaldehyde of the formula (III)

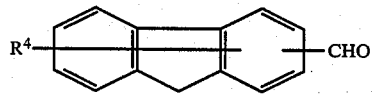

which is then made to react with alkylketone or its equivalent to give a compound of the formula (IV)

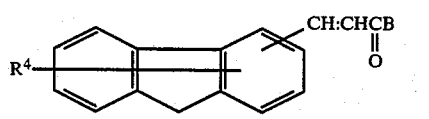

and which is then reduced to give a compound of a formula (V) or (VI)

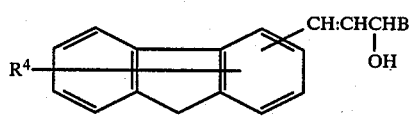

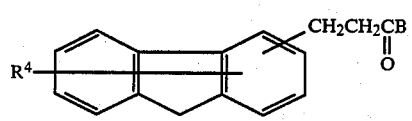

and, when $R^4$ is hydrogen, which compound is, if desired, further treated so as to introduce nitro, amino, hydroxyl, alkoxy (with 1 to 4 carbon atoms), alkyl (with 1 to 4 carbon atoms), or halogen substituent therein to give a compound of a formula (VII) or (VIII)

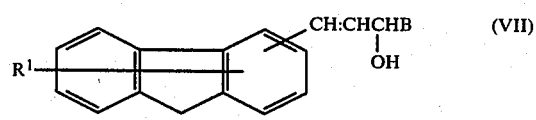

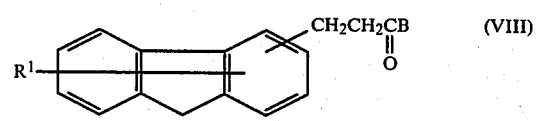

and, in case the product is (IV), (VI) or (VIII), said compound is further reduced, oxidized, acylated or made to react with Grignard reagent to give the desired product (I).

Compounds covered by the present invention are, for example, as follows:
1. 4-(7-Chloro-2-fluorenyl)-3-buten-2-one
2. 4-(2-Methoxy-3-fluorenyl)-3-buten-2-one
3. 4-(7-Methyl-2-fluorenyl)-3-buten-2-ol
4. 4-(2-Fluorenyl)-3-buten-2-ol
5. 4-(7-Chloro-2-fluorenyl)-3-buten-2-ol
6. 4-(2-Fluorenyl)-butan-2-one
7. 4-(7-Methyl-2-fluorenyl)-butan-2-one
8. 4-(7-Chloro-2-fluorenyl)-butan-2-one
9. 4-(7-Nitro-2-fluorenyl)-butan-2-one
10. 4-(7-Amino-2-fluorenyl)-butan-2-one
11. 4-(7-Hydroxy-2-fluorenyl)-butan-2-one
12. 4-(7-Methoxy-2-fluorenyl)-butan-2-one
13. 4-(2-Methoxy-3-fluorenyl)-butan-2-one
14. 4-(2-Fluorenyl)-butan-2-ol
15. 4-(7-Methyl-2-fluorenyl)-butan-2-ol
16. 4-(7-Chloro-2-fluorenyl)-butan-2-ol
17. 4-(7-Nitro-2-fluorenyl)-butan-2-ol
18. 4-(7-Hydroxy-2-fluorenyl)-butan-2-ol
19. 4-(7-Methoxy-2-fluorenyl)-butan-2-ol
20. 4-(2-Methoxy-3-fluorenyl)-butan-2-ol
21. 4-(2-Fluorenyl)-pentan-2-ol
22. 4-(2-Fluorenyl)-pentan-2-one
23. 4-(9-Oxo-2-fluorenyl)-butan-2-one
24. 4-(9-Oxo-2-fluorenyl)-butan-2-ol
25. 4-(2-Fluorenyl)-butan-2-ol acetate
26. 4-(9-Oxo-2-fluorenyl)-butan-2-ol acetate
27. 4-(2-Fluorenyl)-2-methylbutan-2-ol
28. 1-(7-Nitro-2-fluorenyl)-heptan-3-ol acetate Pharmacological experimental data of representative compounds of the present invention are as follows.

TEST METHODS (Effect on carrageenin edema)

One group consisting of 5 male rats of SD strain and of five weeks age was used in the experiment. Compounds to be tested were given orally and, three hours thereafter, 0.1 ml of 0.5% λ-carrageenin was injected at the right hind paw subcutaneously.

After three hours, volume of the right hind paw was measured using a plethysmometer, then the volume of the hind paw before the carrageenin injection was deducted from the above measured value to obtain the degree of swelling (in ml), the average swelling inhibition rate of the groups treated with the compounds as compared with the control group was calculated and, using a method of least squares, $ED_{30}$ was determined.

(Action for formation of ulcer)

Male rats (SD strain) of five weeks age were fasted for 24 hours and the test compound (as a suspension in CMC; 0.5% concentration) was given orally at a dose of 1 ml/100 g body weight. After 24 hours, 5% pontamine sky blue (0.5 ml) was injected intravenously and, ten minutes thereafter, the rats were killed by anesthetizing with ether and their stomachs were removed therefrom. About 6 ml of 5% formaline was introduced into the stomach to fix and the state of formation of ulcer was observed with a binocular lens. When at least one ulcer was observed, the ulcer formation was decided to be positive and, according to a Weil's method (four rats per group), $UD_{50}$ (50% ulcer-forming dose) was determined.

(Acetic acid Writhing Method)

Ten male mice (ddY strain) of six weeks age were used as one group. Test compounds were given orally and, three hours later, 0.1 ml/10 g of 0.6% acetic acid was given intraperitoneally. The total writhing numbers observed from the administration to 20 minutes thereafter were counted and, from the total writhing numbers of the control group, the inhibition rate was determined and, by a method of least squares, $ED_{30}$ was calculated.

(Acute Toxicity)

Four male rats (SD strain) of six weeks age were used as a group and the $LD_{50}$ values seven days after oral administration was calculated by Weil's method.

(Antipyretic action)

Ten male rats (SD strain) of six weeks age were used as a group and made run a fever by subcutaneous injection of 20% brewer's yeast (10 ml/kg). Test compounds were given orally 18 hours after the yeast injection and the body temperature at rectum was observed by a digital electronic thermometer at 1, 3 and 5 hours thereafter.

The following data were obtained, which show the activity of the compounds (I) of the invention as compared to indomethacin as a control:

| Compounds Tested (Example Number) | Inhibition against Carrageenin edema $ED_{30}$ in mg/kg rats, p.o. | Inhibition against Acetic acid writhing $ED_{30}$ in mg/kg mice, i.p. | Antipyretic action mg/kg rats | $UD_{50}$ mg/kg rats, p.o. | $LD_{50}$ mg/kg rats, p.o. |
| --- | --- | --- | --- | --- | --- |
| 2 | 28.3 | 1.8 | 50 | 90.0 | 1682 |
| 3 | 12.5 | 37.2 | 50 | 182.2 | >2000 |
| 9 | 17.3 | 18.4 | <20 | 68.4 | >2000 |
| Indomethacin | 7.1 | 2.3 | 10 | 4.0 | 29.0 |

Compounds (I) of the invention may be administered to animals, including humans, as such, but usually they will be in the form of a pharmaceutical composition comprising from about 0.1 to about 99.5%, preferably from about 0.5 to about 90%, of compound (I) in combination with a pharmaceutically acceptable, non-toxic, inert carrier.

Examples of useful carriers are one or more solid, semi-solid or liquid diluents, fillers and other pharmaceutical auxiliary agents. It is desired that the pharmaceutical compositions are administered as a unit dosage form. The present invention pharmaceutical preparations may be administered per os, into tissue, locally (such as via skin) or rectally. Of course, the administration is conducted by a form suitable for each route. For instance, oral administration is especially preferred.

It is desired that the dose is regulated after considering the state of the patient, such as age, body weight, etc., administration route, and the nature and degree of the disease but usually the daily dosage will be in the range of from about 0.1 to 1,000 mg. A suitable dosage may also be expressed as being in the range of from about 0.001 to about 40 mg/kg of bodyweight of the animal, including humans, to which compound (I) is administered. Of course, in some cases, the dosage may have to be adjusted to be above or below the dosage ranges set forth above. When a large amount is given, it is desired that the compound is administered, in divided dosages, i.e. several times a day.

Oral administration is carried out by a solid or liquid dose unit form such as, for example, pure powder, diluted powder, tablets, sugar coated tablets, capsules, granules, suspensions, liquid, syrups, drops, sublingual tablets and other forms.

Pure powder is manufactured by making active substance into suitable fine size.

Diluted powder is manufactured by making the active substance into suitable fine size and the mixed with similarly fine carriers such as starch, mannitol and other edible hydrocarbons and others. If necessary, seasoning agents, preservatives, dispersion agents, colouring agents, perfumes, and others may be mixed therewith.

Capsules are manufactured as follows. Thus, the pure powder or diluted powder in powdery form as above or the granules as illustrated in the entry of tablets are filled in outer capsules such as, for example, gelatine capsule. It is of course possible to mix the powdery substances with lubricants or fluidizing agents such as, for example, colloidal silica, talc, magnesium stearate, calcium stearate, solid polyethylene glycol and the like followed by conducting the filling operation. Addition of disintegrating agents or solubilizing agents such as, for example, carboxy methyl cellulose, carboxy methyl cellulose calcium, hydroxypropyl cellulose with low degree of substitution, calcium carbonate, sodium carbonate and the like is effective in improving the effectiveness of the pharmaceuticals when capsules are taken.

Finely powdered compound of the present invention may also be suspended and dispersed in vegetable oil, polyethylene glycol, glycerine, surface active agents, and the like and packed with gelatine sheets to afford soft capsules.

Tablets are manufactured by first preparing powdery mixture, then made into granules or slugs, mixed with disintegrating agents or lubricants, and then made into tablets.

Powdery mixtures are prepared by mixing a suitably pulverized substance with the above-given diluents or bases followed, if necessary, by mixing with combining agents (such as sodium carboxy methyl cellulose, alginates, gelatine, polyvinyl pyrrolidone, polyvinyl alcohol and the like), solubilization retarding agents (such as paraffine), reabsorbing agents (such as quaternary salts) and/or absorbing agents (such as bentonite, kaolin, dicalcium phosphate and the like). Powdery mixtures may be made into granules by first wetting with combining agents such as syrup, starch paste, gum arabicum, cellulose solution or polymer solution followed by a compulsory passing through a sieve. Instead of granulating the powder as such, the powder may be first treated with a tablet machine and then pulverizing the obtained slugs of various forms to give granules.

Granules thus prepared are mixed with lubricants such as stearates, stearic acid, talc, mineral oil and others whereupon it is possible to prevent adherence each other. Such a lubricated mixture is then compressed to make tablets. Alternatively, the active substances are, without granulation and making into slugs, directly compressed into tablets after mixing with fluidizing inert carriers. Transparent or semitransparent protective coatings comprising closed shellac membrane, coatings of sugar or polymers, and brushing up coatings comprising waxes may also be used.

Other preparation forms for oral administration such as solutions syrups, elixiers, and the like may also be in a dosage unit form in which its definite amount contains definite amount of the pharmaceutically active substance. Syrups are manufactured by dissolving a compound in a suitable aqueous solution of sweetening agent and perfumes. Elixiers are prepared by the use of non-toxic alcoholic carriers. Suspensions are prepared by dispersing the compound in non-toxic carriers. If necessary, solubilizing agents and emulsifying agents (such as ethoxylated isostearyl alcohols, polyoxyethylene sorbitol esters, etc), preservatives, seasoning agents (such as peppermint oil, saccharine, etc.) and others may also be added.

If necessary, dose unit forms for oral administration may be made into microcapsules. Said form may also be coated and embedded in polymers or wax so that prolongation of acting time or sustained released effect can be resulted.

Parenteral administration can be done by the use of liquidal dosage unit forms (such as solution or suspension) suitable for subcutaneous, intramuscular or intravenous injections. They are manufactured first by suspending or dissolving a definite amount of the compound in non-toxic liquid carriers suitable for each injection purpose such as aqueous or oily medium and then by sterilizing said suspension or solution. Alternatively, a definite amount of the compound is taken into vials and then the vial together with the content therein are sterilized and sealed. In order to make the substance dissolved or mixed immediately before administration, preliminary or auxiliary vials or carriers may be prepared in addition to pulverized or lyophilized effective constituent. In order to make the injection solution isotonic, non-toxic salt or a solution thereof may be added thereto. Further, stabilizers, preservatives, emulsifiers, and the like may be simultaneously applied.

Rectal administration can be conducted by the use of suppositories in which the compound is mixed with a lower melting solid (which is soluble or insoluble in water) such as, for example, polyethylene glycol, cacao butter, higher esters (such as myristyl palmitate) or a mixture thereof.

The manufacturing method of the present invention compounds will be further illustrated as hereunder by way of various examples.

Example for Reference

A mixture of 14.5 grams of fluorene-2-carboxaldehyde and 28.5 grams of acetylmethylidene triphenylphosphoran was dissolved in 400 ml of benzene and heated to reflux for 24 hours. Benzene was evaporated from the reaction mixture and the residue was recrystalized from ethanol to give 14.6 grams of 4-(2-fluorenyl)-3-buten-2-one, m.p. 146° to 147.5° C. as white crystals Elementary analysis calculated for $C_{17}H_{14}O$: C 87.14, H 6.02; found C 87.31, H 5.85.

EXAMPLE 1

Similarly prepared were the following compounds using 7-substituted fluorene-2-carboxaldehyde or 2-substituted fluorene-3-carboxaldehyde as starting materials in place of fluorene-2-carboxaldehyde in the above Example for Reference.

4-(7-Chloro-2-fluorenyl)-3-buten-2-one: m.p. 122°–123° C. Elementary analysis (%) calculated for $C_{17}H_{13}ClO$: C 75.98, H 4.88; found: C 76.18, H 4.71.

4-(2-Methoxy-3-fluorenyl)-3-buten-2-one: m.p. 173° C. Elementary analysis (%) calculated for $C_{18}H_{16}O_2$: C 82.06, H 6.10, Found: C 81.79, H 6.08.

EXAMPLE 2

To 200 ml of methanol was added 9.36 grams of 4-(2-fluorenyl)-3buten-2-one, then 14.9 grams of cerous chloride (heptahydrate) was added, and 1.52 grams of sodium borohydride was added thereto little by little with ice-cooling and stirring. After being stirred for 45 minutes, methanol was removed therefrom by evaporation, water was added to the residue, and extracted with chloroform. The extract was washed with water, dehydrated with magnesium sulfate, and chloroform was evaporated therefrom. The residue was recrystallized from methanol to give 7.3 grams of 4-(2-fluorenyl)-3-buten-2-ol, white crystals, melting point 153° C.

Elementary analysis calculated for $C_{17}H_{16}O$: C 86.40, H 6.82, Found: C 86.54, H 7.00.

In place of the above 4-(2-fluorenyl)-3-buten-2-one, the corresponding 4-(7-substituted 2-fluorenyl)-3-buten-2-one was used and the similar treatment was conducted to give the following compounds.

4-(7-Methyl-2-fluorenyl)-3-buten-2-ol: m.p. 158°–160° C. Elementary analysis calculated for $C_{18}H_{18}O$: C 86.36, H 7.25; Found: C 86.39, H 7.33.

4-(7-Chloro-2-fluorenyl)-3-buten-2-ol; m.p. 150°–152° C. Elementary analysis calculated for $C_{17}H_{15}ClO$: C 75.41, H 5.58; Found: C 75.42, H 5.42.

EXAMPLE 3

To 350 ml of ethyl acetate were added 17 grams of 4-(2-fluorenyl)-3-buten-2-one and 2 grams of 10% palladium carbon powder, the mixture was warmed at 40°–50° C., and hydrogen was introduced in under ordinary pressure. When the absorption of hydrogen ceased, the catalyst was removed by filtration, the filtrate was concentrated, and ethyl acetate was removed therefrom. Crystals separated out therefrom were recrystallized from methanol to give 9.65 grams of 4-(2-fluorenyl)-butan-2-one, white crystals, m.p. 99°–101° C.

Elementary analysis calculated for $C_{17}H_{16}O$: C 86.40, H 6.82; Found: C 86.37, H 6.76.

Similarly were prepared the following compounds starting from the corresponding 4-(7-substituted 2-fluorenyl)-3-buten-2-one or 4-(2-substituted 3-fluorenyl)-3-buten-2-one in place of the above 4-(2-fluorenyl)-3-buten-2-one.

4-(7-Methyl-2-fluorenyl)-butan-2-one: m.p. 80° C. Elementary analysis calculated for $C_{18}H_{18}O$: C 86.36, H 7.25; Found: C 86.46, H 7.28.

4-(2-Methoxy-3-fluorenyl)-butan-2-one: m.p. 103°–104° C. Elementary analysis calculated for $C_{18}H_{18}O_2$: C 81.17, H 6.81. Found: C 81.16, H 6.88.

EXAMPLE 4

In 50 ml of acetic acid was suspended 5.90 grams of 4-(2-fluorenyl)-butan-2-one and 6.35 ml of concentrated nitric acid was dropped in during 45 minutes with stirring at room temperature. After stirring for 3 hours and 30 minutes, crystals separated out therefrom were collected by filtration, washed with small amount of acetic acid, and washed with water until the washing became neutral. The resulting crystals were dissolved in 250 ml of chloroform, dried over magnesium sulfate, and chloroform was evaporated therefrom in vacuo. The residue was recrystallized from benzene to give 3.83 grams of 4-(7-nitro-2-fluorenyl)-butan-2-one, yellow crystals, m.p. 159°–161.5° C.

Elementary analysis calculated for $C_{17}H_{15}O_3N$: C 72.58, H 5.37, N 4.98; Found: C 72.52, H 5.34, N. 4.98.

EXAMPLE 5

To 400 ml of methanol were added 5.62 grams of 4-(7-nitro-2-fluorenyl)-butan-2-one and 280 mg of platinic oxide (monohydrate) and subjected to catalytic reduction at ordinary pressure. The catalyst was removed by filtration and methanol was removed by evaporation in vacuo. To the residue was added small amount of methanol and the crystals separated out were collected by filtration to give 4-(7-amino-2-fluorenyl)-butan-2-one, m.p. 116°–117° C.

EXAMPLE 6

In 50 ml of water was suspended 3.78 grams of 4-(7-amino-2-fluorenyl)-butan-2-one, 4 ml of concentrated hydrochloric acid was added with stirring, and 50 ml of water was added thereto. The reaction solution was cooled with ice and a solution of 1.04 grams of sodium nitrite in 10 ml of water was dropped in during 45 minutes with stirring. After the dropping was completed, the mixture was gradually made to room temperature. The resulting diazonium salt solution was dropped, during 30 minutes, into a stirring and refluxing mixture of cuprous chloride (equimolar to the amine) prepared by known method and 50 ml of water. The mixture was heated to reflux for two hours, allowed to cool, and crystals separated out therefrom were collected by filtration.

The crystals were dissolved in chloroform and the solution was dried with magnesium sulfate. This was subjected to a silicagel column chromatography, crystals obtained by eluting with a 4:1 mixture of n-hexane and ethyl acetate was recrystallized from methanol, and 1.70 grams of 4-(7-chloro-2-fluorenyl)-butan-2-one, m.p. 72.5°–73.5° C., were obtained as white crystals.

Elementary analysis calculated for $C_{17}H_{15}ClO$: C 75.41, H 5.58; Found: C 75,46, H 5.44.

EXAMPLE 7

Diazonium salt was prepared by the same way as in Example 6 using 6.47 grams of 4-(7-amino-2-fluorenyl)-butan-2-one. The diazonium salt was dropped into a refluxing and stirring mixture of 9 ml of concentrated sulphuric acid and 150 ml of water. After being stirred for 2 hours, the mixture was cooled and crystals separated out therefrom were collected by filtration. They were washed until the washing became neutral and dried with air. The resulting crystals were subjected to a silica gel column chromatography, eluted with a 4:1 mixture of n-hexane and ethyl acetate, and the resulting crystals were recrystallized from methanol to give 4.96 grams of 4-(7-hydroxy-2-fluorenyl)-butan-2one, pale yellow crystals, m.p. 170°–170.5° C.

Elementary analysis calculated for $C_{17}H_{18}O_2$: C 80.92, H 6,39; Found: C 80.92, H 6.33.

EXAMPLE 8

In 50 ml of acetone was dissolved 2.17 grams of 4-(7-hydroxy-2-fluorenyl)-butan-2-one, then 1.43 grams of potassium carbonate (anhydrous) was added, and heated to reflux for 2 hours after addition of an excess of methyl iodide. The mixture was stirred at room temperature for overnight and acetone was removed by evaporation in vacuo. The residue was dissolved in ethyl acetate, washed with water, dried with magnesium sulfate, and ethyl acetate was removed therefrom by evaporation in vacuo. The residue was subjected to a silica gel column chromatography, eluted with a 4:1 mixture of n-hexane and ethyl acetate, and the resulting crystals were recrystallized from methanol to give 1.15 grams of 4-(7-methoxy-2-flourenyl)-butan-2-one, white crystals, m.p. 100°–101° C.

Elementary analysis calculated for $C_{18}H_{18}O_2$: C 81.17, H 6.81; Found: C 81.16, H 6.80.

EXAMPLE 9

To 200 ml of methanol was added 11 grams of 4-(2-fluorenyl)-butan-2-one, the mixture was cooled with ice, and 1.32 grams of sodium borohydride was slowly added thereto with stirring. After being stirred for one hour, methanol was removed therefrom by evaporation in vacuo, to the residue was added water, and the mixture was extracted with chloroform. The extract was washed with water, dried with magnesium sulfate, and the solvent was evaporated. The residue was recrystallized from ethyl acetate to give 9.6 grams of 4-(2-flourenyl)-butan-2-ol, white crystals, m.p. 120°–121° C.

Elementary analysis calculated for $C_{17}H_{18}O$: C 85.67, H 7.61; Found: C 85.61, H 7.54.

Similarly prepared were the following compounds starting from the corresponding 4-(7-substituted 2-fluorenyl)-butan-2ones or 4-(2-substituted 3-fluorenyl)-butan-2-ones in place of the above 4-(2-fluorenyl)-butan-2one.

4-(7-Methyl-2fluorenyl)-butan-2-ol: m.p. 123° C. Elementary analysis calculated for $C_{18}H_{20}O$: C 85.67, H 7.99; Found: C 85.71, H 7.99.

4-(7-Chlor-2-fluorenyl)-butan-2ol: m.p. 118°–120° C. Elementary analysis calculated for $C_{17}H_{17}OCl$: C 74.86, H 6.28; Found: C 74.83; H 6.17.

4-(7-Nitro-2-fluorenyl)-butan-2-ol: m.p. 110°–122° C. Elementary analysis calculated for $C_{17}H_{17}O_3N$: C 72.06, H 6.05. N 4.94; Found: C 72.01, H 6.02, N. 4.94.

4-(7-Hydroxy-2-fluorenyl)-butan-2ol: m.p. 170°–170.5° C. Elementary analysis calculated for $C_{17}H_{18}O_2$: C 80.28, H 7.13; Found: C 80.37, H 7.15.

4-(7-Methoxy-2-fluorenyl)-butan-2-ol: m.p. 142°–143.5° C. Elementary analysis calculated for $C_{18}H_{20}O_2$: C 80.56, H 7.51; Found: C 80.69, H 7.61.

4-(2-Methoxy-3-fluorenyl)-butan-2-ol: m.p. 129°–130° C. Elementary analysis calculated for $C_{18}H_{20}O_2$: C 80.56, H 7.51; Found: C 79.98, H 7.60. EXAMPLE

EXAMPLE 10

Methyl magnesium iodide was synthesized from 0.73 gram of magnesium, 4.23 grams of methyl iodide and anhydrous ether in an argon stream. To this was added 5.01 grams of cuprous iodide and the mixture was stirred. A suspension of 5.85 grams of 4-(2-fluorenyl)-3-buten-2-one in 50 ml of tetrahydrofuran was slowly added to the above stirring above mixture at room temperature. After being stirred for 30 minutes, the mixture was mixed with water, ethyl acetate was added thereto, the organic solvent layer was washed with water, and dried with magnesium sulfate. The residue was subjected to a silica gel chromatography (column), the column was eluted with chloroform, and yellowish brown oily product was obtained. This was distilled to give 0.70 gram of 4-(2-fluorenyl)-pentan-2-one, yellow crystals, m.p. 72°–74° C.

Elementary analysis calculated for $C_{18}H_{18}O$: C 86.36, H 7.24; Found: C 86.41, H 7.21.

EXAMPLE 11

Methyl magnesium iodide was synthesized from 0.73 gram of magnesium, 4.23 grams of methyl iodide and 20 ml of anhydrous ether in an argon stream. A solution of 5.9 grams of 4-(2- fluorenyl)-butan-2-one in a mixture of 20 ml of ether and 40 ml of tetrahydrofuran was dropped into the above mixture at room temperature. The mixture was stirred for one hour at room temperature and aqueous solution of ammonium chloride was added. Chloroform was added thereto and extracted. The extract was washed with water and dried with magensium sulfate. Chloroform was evaporated therefrom by evaporation, the residue was subjected to a medium pressure liquid chromatography, eluted with chloroform, and recrystallized from ethyl acetate to give 2.4 grams of 4-(2-fluorenyl)-2-methylbutan-2ol, m.p. 116°–117° C.

Elementary analysis calculated for $C_{18}H_{20}O$: C 85.67, H 7.98; Found: C 85.51, H 7.98.

EXAMPLE 12

4-(2-Fluorenyl)-butan-2-one (4.72grams) was dissolvedin a mixture of 60 ml of pyridine and 5 ml of water, the mixture was heated at 60° C., and stirred. Potassium permanganate (6.8 grams) was added thereto little by little during 2 hours. When the addition was finished, the mixture was stirred for 2 hours more. The reaction solution was filtered, the filtrate was concentrated, and the resulting residue was dissolved in chlroform, the solution was washed with in the order of 10% hydrochloric acid, water, saturated sodium bicarbonate, and water, then dried with magensium sulfate, the solvent was evaporated therefrom, and the residue was recrystallized from ethanol to give 1.3 grams of 4-(9-oxo-2fluorenyl)-butan-2-one, yellow crystals, m.p. 75°–77° C.

Elementary analysis calculated for $C_{17}H_{14}O_2$: C 81.58, H 5.64; Found: C 81.63, H 5.44.

Similarly prepared was 2.56 grams of 4-(9-oxo-2fluorenyl)-butan-2ol acetate starting from 4-(2-fluorenyl)-butan-2-ol acetate in place of the above 4-(2-fluorenyl)-butan-2-one.

Elementary analysis calculated for $C_{19}H_{18}O_3$: C 77.53, H 6.16; Found: C 77.73, H 6.09.

EXAMPLE 13

To 4.72 grams of 4-(2-fluorenyl)-butan-2-ol were added 1.74 grams of pyridine and 2.24 grams of acetic anhydride and the mixture was heated to reflux for 25 hours. An excess of acetic anhydride and pyridine was removed by evaporation, the residue was subjected to a silica gel column chromatography, the column was eluted with a 4:1 mixture of n-hexane and ethyl acetate, and the resulting crystals were recrystallized from n-hexane to give 5 grams of 4-(2-fluorenyl)-butan-2-ol acetate, white crystals, m.p. 63°–64.5° C.

Elementary analysis calculated for $C_{19}H_{20}O_2$: C 81.39, H 7.19; Found: C 81.05, H 7.28.

EXAMPLE 14

Sodium hydroxide (0.2 gram) was dissolved in a mixture of 20 ml of methanol and 5 ml of water, then 1.47 grams of 4-(9-oxo-2-fluorenyl)-butan-2-ol acetate was added thereto, and the mixture was heated to reflux for two hours. After removal of methanol by evaporation therefrom, chloroform was added to the residue, the mixture was washed with water, and dried with magnesium sulfate. Chlorform was evaporated therefrom and the residue was allowed to stand to give crystals. They were recrystallized from isopropyl ether to give 1.2 grams of 4-(9-oxo-2-fluorenyl)-butan-2-ol, yellow crystals, m.p. 77°–78° C.

Elementary analysis calculated for $C_{17}H_{16}O_2$: C 80.93, H 6.39; Found: C 81.19, H 6.34.

We claim:

1. A compound of the formula (I)

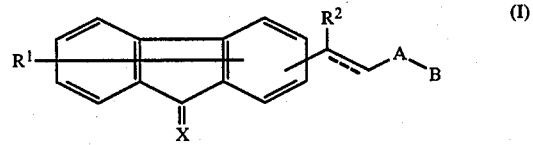

in which $R^1$ is hydrogen, nitro, amino, hydroxyl, alkoxy of one to four carbon atoms, alkyl of one to four carbon atoms or halogen; $R^2$ is hydrogen or alkyl of one to four carbon atoms; ========= is a saturated or unsaturated bond; A is CO, CHOH, $C(R^5)OH$ or $CHOCOR^6$, where $R^5$ and $R^6$ are alkyl of one to four carbon atoms; B is alkyl of one to twelve carbon atoms; and X is $H_2$ or O.

2. A compound according to claim 1, in which $R^1$ is hydrogen, alkoxy of one to four carbon atoms or halogen; $R^2$ is hydrogen; ========= is an unsaturated bond; A is CO; B is alkyl of one to twelve carbon atoms; and X is $H_2$.

3. A compound according to claim 1, in which $R^1$ is hydrogen, alkyl of one to four carbon atoms, alkoxy of one to four carbon atoms or halogen; $R^2$ is hydrogen; ≡≡≡≡≡is an unsaturated bond; A is CHOH; B is alkyl of one to twelve carbon atoms; and X is $H_2$.

4. A compound according to claim 1, in which $R^1$ is hydrogen, alkyl of one to four carbon atoms, alkoxy of one to four carbon atoms or halogen; $R^2$ is hydrogen; ≡≡≡≡≡is a saturated bond; A is CO; B is alkyl of one to twelve carbon atoms; and X is $H_2$.

5. A compound according to claim 1, in which $R^1$ is hydrogen, nitro, amino, hydroxyl, alkoxy of one to four carbon atoms, alkyl of one to four carbon atoms or halogen; $R^2$ is hydrogen; ≡≡≡≡≡is a saturated bond; A is CHOH; B is alkyl of one to twelve carbon atoms; and X is $H_2$.

6. A compound according to claim 1, which is 4-(2-fluorenyl)-3-buten-2-ol.

7. A compound according to claim 1, which is 4-(7-methyl-2-fluorenyl)-3-buten-2-ol.

8. A compound according to claim 1, which is 4-(7-chloro-2-fluorenyl)-3-buten-2-ol.

9. A compound according to claim 1, which is 4-(2-fluorenyl)-butan-2-one.

10. A compound according to claim 1, which is 4-(7-methyl-2-fluorenyl)-butan-2-one.

11. A compound according to claim 1, which is 4-(2-methoxy-3-fluorenyl)-butan-2one.

12. A compound according to claim 1, which is 4-(2-fluorenyl)-butan-2-ol.

13. A compound according to claim 1, which is 4-(7-methyl-2-fluorenyl)-butan-2-ol.

14. A compound according to claim 1, which is 4-(7-chlor-2-fluorenyl)-butan-2-ol.

15. A compound according to claim 1, which is 4-(7-nitro-2-fluorenyl)-butan-2-ol.

16. A compound according to claim 1, which is 4-(7-hydroxy-2-fluorenyl)-butan-2-ol.

17. A compound according to claim 1, which is 4-(7-methoxy-2-fluorenyl)-butan-2-ol.

18. A compound according to claim 1, which is 4-(2-methoxy-3fluorenyl)-butan-2-ol.

19. A method of obtaining an anti-inflammatory, analgesic and/or anti-pyretic effect in animal, including humans, in need thereof, which comprises administering to said animal an effective amount of a compound according to claim 1.

20. A pharmaceutical composition for use in obtaining an anti-inflammatory, analgesic and/or anti-pyretic effect in an animal, including humans, in need thereof, which comprises an effective amount of a compound according to claim 1, in combination with a pharmaceutically acceptable carrier.

* * * * *